United States Patent [19]

Mitchell et al.

[11] Patent Number: 4,704,485
[45] Date of Patent: Nov. 3, 1987

[54] HYDROHALOGENATION OF MYRCENE

[75] Inventors: Peter W. D. Mitchell, Freehold, N.J.; Lois T. McElligott, Abington, Pa.; David E. Sasser, Jacksonville, Fla.

[73] Assignee: Union Camp Corporation, Wayne, N.J.

[21] Appl. No.: 750,925

[22] Filed: Jul. 1, 1985

Related U.S. Application Data

[63] Continuation-in-part of Ser. No. 515,562, Jul. 20, 1983, abandoned.

[51] Int. Cl.[4] ............................................. C07C 17/08
[52] U.S. Cl. .................................................... 570/231
[58] Field of Search .............................. 570/231, 236

[56] References Cited

U.S. PATENT DOCUMENTS

| | | | |
|---|---|---|---|
| 2,242,084 | 5/1941 | Nicodemus | 570/236 |
| 2,609,388 | 9/1952 | Knapp et al. | 570/231 |
| 2,871,271 | 1/1959 | Booth | 570/231 |
| 3,016,408 | 1/1962 | Webb | 570/231 |
| 3,055,954 | 9/1962 | Montagna et al. | 570/231 |
| 3,819,730 | 6/1974 | Nakata et al. | 570/236 |
| 3,836,592 | 9/1974 | Gordon | 570/236 |
| 3,993,586 | 11/1976 | Hagedorn et al. | 570/231 |

Primary Examiner—J. E. Evans
Assistant Examiner—Joseph A. Boska
Attorney, Agent, or Firm—Kane, Dalsimer, Sullivan, Kurucz, Levy, Eisele and Richard

[57] ABSTRACT

The disclosure is of an improved process for the hydrohalogenation of a conjugated diene in the presence of a catalyst, which comprises carrying out the hydrohalogenation in the presence of an organic quaternary salt.

10 Claims, 1 Drawing Figure

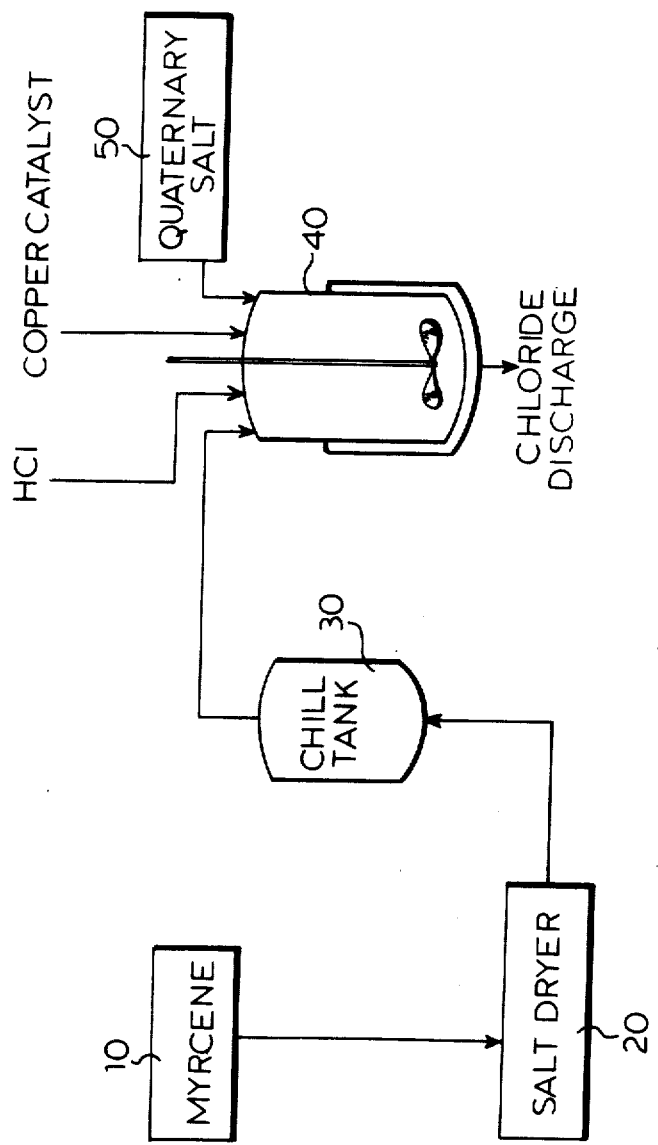

HYDROHALOGENATION OF MYRCENE

CROSS-REFERENCE TO RELATED APPLICATION

This application is a continuation-in-part of copending U.S. application Ser. No. 515,562 filed July 20, 1983, now abandoned.

BACKGROUND OF THE INVENTION

1. Field of the Invention

The invention related to processes for the hydrohalogenation of myrcene.

2. Brief Description of the Prior Art

The literature is replete with descriptions of processes for the hydrohalogenation of conjugated dienes. Representative of such descriptions are those found in the U.S. Pat. Nos. 2,882,323 and 3,016,408 and in British Pat. No. 896,262.

The present invention is particularly advantageous when used to hydrochlorinate myrcene. Myrcene is a conjugated diene of the formula:

(I)

When hydrochlorinated in the absence of any catalyst, the major product is myrcenyl chloride. However, the commercially valuable products of myrcene hydrochlorination are the associated co-products, namely, geranyl chloride and neryl chloride. Hydrochlorination in the presence of a copper-containing catalyst shifts the reaction in faor of the desired co-products. It has been-postulated that the hydrochlorination of myrcene in the presence of a copper catalyst proceeds according to the reaction scheme:

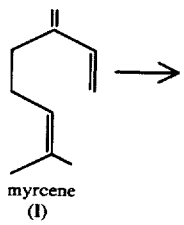

myrcene
(I)

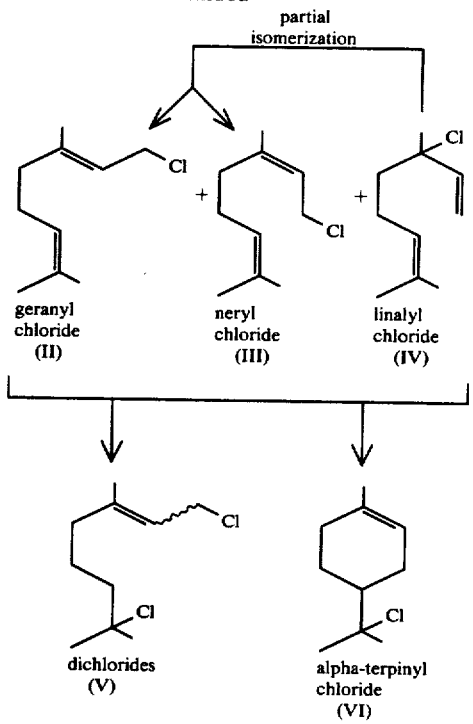

Cyclization may also undesirably occur to form the alpha-terpinyl chlorides.

When the copper catalyst employed is in the form of cupric chloride ($CuCl_2$) the products generally include substantial proportions of linalyl chloride and lesser proportions of the desired geranyl and neryl chlorides. When the copper catalyst is in the form of cuprous chloride, the linalyl chloride product is lessened due, apparently, to partial isomerization to the desired geranyl, and neryl chlorides.

From the above proposed reaction scheme, it will be appreciated that any process for hydrochlorination of myrcene, to be commercially feasible, must result in a favorable yield of the desired geranyl (II) and neryl (III) monochlorides and minimal formation of linalyl (IV) and alpha-terpinyl (VI) monochlorides. It was previously appreciated that the relative proportions of monochlorides (II), (III) and (IV) in the hydrochlorination product reaction mixture could be controlled to some degree by selection of the reaction temperature, gas flowrate and catalyst concentration.

We have now found that when the prior art hydrohalogenation of myrcene (U.S. Pat. No. 3,016,408 to Webb and U.S. Pat. No. 2,871,271 to Booth), is carried out in the presence of a of catalytic amount of a certain kind of organic quaternary salt, then the isomerization of the linalyl chloride product during the hydrohalogenation reaction is shifted to favor formation of the less-substituted allylic chloride, being geranyl chloride (II) and neryl chloride (III).

While it is known in the prior art to employ a copper catalyst in combination with an organic quaternary salt (U.S. Pat. Nos. 3,819,730 to Nakata and 3,836,592 to Gordon) to isomerize an allylic halide to its allylic isomer in a separate reaction step, apart from the formation of the allylic halide by hydrohalogenation of a diene, the shortcomings of the art are evident when applied to the isomerization of linalyl chloride, in particular the use of elevated temperatures which product low yields because of extensive rearrangement to terpinyl chloride, an indesirable side reaction unique to the myrcene hydrochlorides.

The advantages associated with the improved process of the invention are improved overall yield of the more desirable neryl and geranyl chlorides and a greater selectivity of the more important geranyl isomer. Furthermore, because isomerization occurs during the hydrochlorination operation, there is no need for a subsequent, separate isomerization operation.

SUMMARY OF THE INVENTION

The invention comprises, a novel method for the hydrohalogenation of myrcene comprising hydrohalogenating myrcene under anhydrous, liquid conditions in the presence of a copper-containing hydrohalogenation catalyst, and further comprising carrying out the hydrohalogenation at a temperature below 25° C. in the presence of an organic quaternary salt which has a carbon atom content of at least 18.

The improved process of the invention may be carried out in a batch or a continuous manner.

BRIEF DESCRIPTION OF THE DRAWING

The accompanying drawing is a schematic representation of a preferred embodiment process of the invention.

DETAILED DESCRIPTION OF THE PREFERRED EMBODIMENTS OF THE INVENTION

The method of the invention is employed advantageously for the hydrohalogenation of myrcene to obtain the geranyl and neryl halides which are intermediates for the manufacture of commercially valuable geraniol and nerol. The improved method of the invention will increase the overall yield of the geranyl and neryl halides by at least 11 to 12 mole percent over the prior art processes and will improve selectivity of the ratio of geranyl isomer to the neryl isomer from about 1.3 to 1.6. Commercially available myrcene made by pyrolysis of beta-pinene, purified forms of myrcene, and myrcene isolated from natural materials may be provided as the starting material in the preferred process of the invention.

The accompanying drawing is a schematic representation of a preferred embodiment method of the invention for the hydrochlorination of myrcene. As shown in the FIGURE the provided myrcene initially held in tank 10 may be first dried in conventional salt bed dryer 20 to remove water, as necessary. The dried myrcene is then preferably cooled to a temperature in the range of from about −30° C. to about 25° C.; most preferably circa 10° C. in a cooling unit 30. Alternatively, the myrcene may be cooled first and then processed through a salt bed dryer 20 to remove water. Cooling the starting myrcene prior to drying in the salt bed dryer 20 is somewhat advantageous in that pre-cooling increases drying efficiency in the salt bed dryer 20.

As shown in the FIGURE the dried and cooled myrcene starting material may be passed into a hydrohalogenation apparatus which comprises in the preferred embodiment a stirred tank reactor 40. In reactor 40, hydrohalogenation of the introduced myrcene is carried out in the presence of a copper hydrohalogenation catalyst, at a temperature within the range of from about −30° C. to about 25° C., most preferably within the range of from −10° C. to 25° C., most preferably about 10° C. Hydrohalogenation may be effected, for example, by reaction of the myrcene with a hydrogen halide like hydrogen chloride or hydrogen bromide, preferably in substantially anhydrous form and under substantially anhydrous conditions, i.e. having less than about 5% water present in the reaction mixture. As shown in the FIGURE, the preferred hydrohalogenation is with gaseous hydrogen chloride which is introduced as a gas, possibly generated in a vaporizer, and then metered into the reactor 40, via appropriate conduits. Advantageously, the hydrogen chloride is metered into the reactor 40 at a rate of from about 2.0 to about 300 gms/hour/mole of myrcene present in the reactor 40. Preferably, the rate is from about 4.0 to 8.0 gm/hour/mole of myrcene.

The organic quaternary salt is introduced into the reactor 40 from storage vessel 50. Myrcene, quaternary salt, hydrogen chloride and copper catalyst are introduced into the reactor 40 sequentially. Preferably, the reactor 40 after purging with an inert gas such as nitrogen is first charged with the cool myrcene, the copper catalyst, and the organic quaternary salt. While cooling and stirring, the hydrogen chloride is added incrementally to the charge.

A wide variety of catalysts for hydrohalogenation of myrcene are well known and include, for example, any copper compound having valency of 2 or less, including metallic copper. Any copper compound convertible to the halide such as the bromide, iodide or chloride under conditions of the reaction may also be used. Representative of copper catalysts advantageously employed are the chloride, bromide, carbonate, oxide, acetate, formate, sulfate, and like derivative cupric and cuprous compounds. Preferred as the hydrochlorination catalyst in the improved process of the invention is cuprous chloride. Catalytic proportions of the anhydrous hydrohalogenation catalyst are generally within the weight range of from about 0.01 to 10 percent of the dry myrcene, preferably about 0.5 percent.

Organic quaternary salts are generally well-known in the art as is their preparation and include quaternary salts and quaternary resins where the central atom is nitrogen, phosphorous or arsenic. Representative of organic quaternary salts which may be used in the process of the invention are those the formula:

(VII)

wherein X is selected from the group consisting of an organic and inorganic anion such as nitrate, benzoate, phenylacetate, hydroxybenzoate, phenoxide, hydroxide, cyanide, nitrite; particularly preferred are chloride, bromide, iodide, methyl sulfate, ethyl sulfate and the like; M represents nitrogen, arsenic, or phosphorous. $R_1$ and $R_2$ and $R_3$ are each independently selected from the group consisting of hydrocarbyl and substituted hydrocarbyl or $R_1$ and $R_2$ may be taken together to represent a divalent moiety attached to the atom M, and which is selected from the group consisting of alkenylene and hydrocarbyl-substituted alkenylene having 5 to 10 carbon atoms, inclusive, in the ring thereof; or $R_1$ and $R_2$ may be taken together with the atom of M to which they are attached to represent a divalent or monovalent moiety selected from the groups consisting of those having the formula:

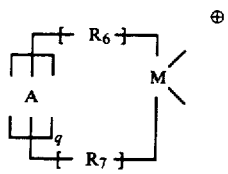

wherein A represents nitrogen, oxygen, sulfur, phosphorous and the like; and $R_6$ and $R_7$ are each selected from alkenylene and hydrocarbyl-substituted alkenylene of 1 to 25 carbon atoms, inclusive; m, n and q are each integers of 0 to 1 and the sum of m+n is 1 or 2.

Organic quaternary salts employed in the method of the invention will have a carbon atom content of at least 18 carbon atoms.

The term "hydrocarbyl" as used herein means the monovalent moiety obtained upon removal of a hydrogen atom from a parent hydrocarbon. Representative of hydrocarbyl are alkyl of 1 to 25 carbon atoms, inclusive, such as methyl, ethyl, propyl, butyl, pentyl, hexyl, heptyl, octyl, nonyl, undecyl, decyl, dodecyl, octadecyl, nonodecyl, eicosyl, heneicosyl, docosyl, tricosyl, tetracosyl, pentacosyl and the isomeric forms thereof; aryl of 6 to 25 carbon atoms, inclusive, such as phenyl, tolyl, xylyl, naphthyl, biphenyl, tetraphenyl and the like, aralkyl of 7 to 25 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 25 carbon atoms, inclusive, such as vinyl, allyl, butenyl, pentenyl, hexenyl, octenyl, nonenyl, decenyl, undececyl, dodecenyl, tridecenyl, pentadecenyl, octadecenyl, pentacosynyl and isomeric forms thereof.

The term "alkenylene" means the divalent moiety obtained on removal of two hydrogen atoms, each from a nonadjacent carbon atom of a parent hydrocarbon and includes alkenylene of 3 to 10 carbon atoms, inclusive, such as 1,3-propenylene, 1,4-butenylene, 1,5-pentenylene, 1,8-octenylene, 1,10-decenylene and the like.

The terms "substituted hydrocarbyl" and "substituted alkenylene" as used herein mean the hydrocarbyl or alkenylene moiety as previously defined wherein one or more hydrogen atoms have been replaced with an inert group, i.e. a chemical group which does not adversely affect the desired function of the organic quaternary salt of formula (VII). Representative of such groups are aminophosphino-, hydrocarbyl, quaternary nitrogen (ammonium), quaternary phosphorous (phosphonium), hydroxyl-, alkoxy, mercapto-, alkyl, halo-, phosphate, phosphite, carboxylate groups and the like.

Organic quaternary compounds of the formula (VII) given above are generally well-known as are methods of their preparation. Representative of such organic quaternary compounds are trioctylmethylammonium chloride, tetraoctadecylammonium chloride, dodecyldimethylbenzyl-ammonium chloride, tetradecyldimethylbenzylammonium chloride, hexadecyldimethylbenzylammonium chloride, trimethylcarboxymethylammonium chloride, triethylgeranylammonium chloride, triethylnerylammonium chloride N,N-cetylethylmorpholinium ethosulfate, methyl(1)cocoamidoethyl(2-)cocoimidazolinium methyl sulfate, N-tallow-pentamethylpropanediammonium dichloride, trioctylmethylphosphonium bromide, N,N-soya ethylmorpholinium ethosulfate, hexadecylpyridinium chloride, triethylbenzylammonium chloride, benzyl hydroxyethyl(2)-cocoimidazolinium chloride, tripropylgeranylammonium chloride, tributylgeranylammonium chloride, doidecyldimethyl(ethylbenzyl)ammonium chloride, tetradecyldimethyl(ethylbenzyl)ammonium chloride, hexadecyldimethyl((ethylbenzyl)ammonium chloride, octadecyldimethyl((ethylbenzyl)ammonium chloride, octadecyldimethylbenzylammonium chloride, methyl bis(2-hydroxyethyl)cocoammonium chloride, methyl(1-)soyaamidoiethyl(2)soyaimidazolinium methyl sulfate, methyl(1)tallowamidoethyl(2)tallow imidazolinium methyl sulfate, methyl(1)oleylamidoethyl(-2)oleylimidazolinium methyl sulfate and the like.

Commercially available quaternary salts or purified forms of quaternary salts may be used in the preferred process of the invention.

It will be appreciated that under specific conditions of operating the process of the invention, certain of the above described compounds of the formula (VII) given above have advantages over other catalysts of the same general formula. Selection of a particular compound (VII) for use under specific process conditions, for optimum yields may be made by trial and error technique. We have observed however that there are advantages associated with a mixture of trialkylmethylammonium chlorides where the alkyl portion consists of a chain of from eight to ten carbon atoms. For example, Adogen 464 (Sherex Chemical Co.) and Aliquat 336 (Henkel Corp.).

The organic quaternary salt is used in a proportion to isomerize, during the hydrohalogenation reaction, at least some of the more-substituted linalyl chloride produced in the method of the invention. Such a proportion is generally within the range of from about 0.01 to 10 percent by weight of myrcene charge, preferably 0.2 to 2.5 percent. Optimum proportions will depend to some extent upon the salt selected and may be determined by trial and error technique.

The controlling reaction rate in the hydrohalogenation process of the invention is the isomerization of the more-substituted linalyl halide to the desired neryl and geranyl halides. This is controlled by residence time in the hydrohalogenation reaction zone. We have found that in hydrochlorination of myrcene, the preferred minimum total residence time is within the range of from 3 to 15 hours, and most preferably 5 to 8 hours under the above described operating temperatures. The presence of linalyl chloride in the reaction mixture may be monitored by conventional analytical techniques. Longer residence times in the hydrochlorination reactor may cause a yield loss due to conversion of the monochlorides to alpha- terpinyl chloride. Shorter residence times may not be sufficient to isomerize the linalyl chloride to the desired geranyl/neryl chlorides.

When it has been determined that hydrohalogenation has occurred to a maximum desired point, the hydrohalogenation product mixture is passed from the hydrohalogenation apparatus.

The following examples describe the manner and the process of making and using the invention and set forth the best mode contemplated by the inventors of carrying out the invention but are not to be construed as limiting. All parts given are by weight unless otherwise indicated.

EXAMPLES

EXAMPLE 1

To a 1 liter reaction vessel was charged 700.0 g myrcene (72 wt %), 2.2 g cuprous chloride and 10.5 g Adogen 464; supra. The mixture was purged with nitrogen and cooled to 0° C. Hydrogen chloride gas was added at a rate of 20 g/hour while maintaining the temperature at 10° C. At the end of the reaction (7 hours), monitored by infrared spectroscopy to a 1% myrcene level, the reaction product was neutralized with sodium carbonate and aqueous sodium hydroxide. The product was analyzed by gas chromatography.

The result of this analysis was as follows: molar yield from myrcene 5 - linalyl chloride 8, geranyl chloride 51, neryl chloride 32, geranyl and neryl chloride ratio - 1.59.

EXAMPLES 2-7

The same starting material used in Example 1 was used and subjected to hydrochlorination under the same conditions as described in Example 1 using 2.2 g cuprous chloride and a quaternary salt as described in Table 1 to obtain the results shown in Table 1. Linalyl, neryl and geranyl chlorides are abbreviated as LCI, NC1 and GC1 respectively.

TABLE 1

| Example No. | Quaternary Salt and Amount Used | Molar Yield of Products (%) | | GCl:NCl Ratio |
|---|---|---|---|---|
| | | LCl | NCl + GCl | |
| 2 | None | 18 | 69 | 1.26 |
| 3 | Benzyldimethylstearyl ammonium chloride, 9.4 g | 8 | 79 | 1.69 |
| 4 | Benzylhydroxyethyl (2) coco imidazolium chloride, 8.2 g | 7 | 73 | 1.40 |
| 5 | Methyltrioctyl- ammonium chloride, 10.5 g | 9 | 74 | 1.52 |
| 6 | Tetra(octadecyl) ammonium bromide, 8.0 g | 16 | 73 | 1.18 |
| 7 | N,N—Cetylethyl- morpholinium etho- sulfate, 10.1 g | 8 | 70 | 1.39 |

What is claimed:

1. A method for the hydrohalogenation of myrcene comprising hydrohalogenating myrcene under anhydrous, liquid conditions in the presence of a copper-containing hydrohalogenation catalyst at a temperature below 25° C. in the presence of an organic quaternary ammonium salt which has a carbon atom content of at least 18.

2. The improved method of claim 1 wherein the organic quaternary salt is benzyldimethylstearylammonium chloride.

3. The improved method of claim 1 wherein the organic quaternary salt is benzylhydroxyethyl(2-)cocoimidazolium chloride.

4. The improved method of claim 1 wherein the organic quaternary salt is tetra(octadecyl)ammonium chloride.

5. The improved method of claim 1 wherein the organic quaternary salt is N,N-cetylethylmorpholinium ethosulfate.

6. The improved method of claim 1 wherein the organic quaternary salt is trioctylmethylammonium chloride.

7. The improved method of claim 1 wherein the organic quaternary salt is a mixture of tri(alkyl)methylammonium chlorides where each alkyl portion is a chain of from eight to ten carbon atoms.

8. The improved process of claim 1 wherein the temperature of reaction is from about −10° C. to about 20° C.

9. The process of claim 1 wherein the hydrohalogenation catalyst is cuprous chloride.

10. The process of claim 9 wherein the catalytic proportion of copper catalyst is within the weight range of about 0.01 to about 10.0 percent of the dry myrcene.

* * * * *

UNITED STATES PATENT AND TRADEMARK OFFICE
CERTIFICATE OF CORRECTION

PATENT NO. : 4,704,485
DATED : November 3, 1987
INVENTOR(S) : Peter W. D. MItchell It is certified that error appears in the above-identified patent and that said Letters Patent is hereby corrected as shown below:

Col. 1, line 51; "faor" should read -- favor -- .

Col. 5, line 5; "[ $R_6$ ]" should read -- [ $R_6$ ]$_m$ -- .

Col. 5, line 10; "[ $R_7$ ]" should read -- [ $R_7$ ]$_n$ -- .

Signed and Sealed this

Fifth Day of July, 1988

Attest:

DONALD J. QUIGG

Attesting Officer

Commissioner of Patents and Trademarks